US012375310B2

(12) United States Patent
Rossignol et al.

(10) Patent No.: US 12,375,310 B2
(45) Date of Patent: Jul. 29, 2025

(54) DAISY CHAINED MARINE SENSOR PLATFORM

(71) Applicant: TidalX AI Inc, San Ramon, CA (US)

(72) Inventors: Andrew Rossignol, Mountain View, CA (US); Eric Teller, San Francisco, CA (US); Laura Valentine Chrobak, Menlo Park, CA (US); Neil Davé, San Mateo, CA (US); Balaprakash Kasiviswanathan, Mountain View, CA (US)

(73) Assignee: TidalX AI Inc., Mountain View, CA (US)

( * ) Notice: Subject to any disclaimer, the term of this patent is extended or adjusted under 35 U.S.C. 154(b) by 880 days.

(21) Appl. No.: 17/507,619

(22) Filed: Oct. 21, 2021

(65) Prior Publication Data

US 2023/0130472 A1     Apr. 27, 2023

(51) Int. Cl.
| | |
|---|---|
| *A01K 61/10* | (2017.01) |
| *G01N 33/18* | (2006.01) |
| *G05B 15/00* | (2006.01) |
| *H04L 12/10* | (2006.01) |

(52) U.S. Cl.
CPC .............. *H04L 12/10* (2013.01); *A01K 61/10* (2017.01); *G01N 33/18* (2013.01); *G05B 15/00* (2013.01)

(58) Field of Classification Search
CPC ........ A01K 79/00; A01K 61/10; H04L 12/10; G01N 33/18; G06F 13/4247; G05B 15/00
See application file for complete search history.

(56) References Cited

U.S. PATENT DOCUMENTS

| | | | |
|---|---|---|---|
| 4,446,538 A | 5/1984 | Zachariadis | |
| 9,429,671 B2 | 8/2016 | Rokkan et al. | |
| 9,791,583 B2* | 10/2017 | Rokkan | ............... G01V 1/3852 |
| 9,995,836 B2* | 6/2018 | Rokkan | ............... G01V 1/3843 |
| 10,856,520 B1 | 12/2020 | Kozachenok et al. | |

(Continued)

FOREIGN PATENT DOCUMENTS

| | | |
|---|---|---|
| CL | 2019000039 A1 | 3/2019 |
| CN | 108040948 | 5/2018 |

(Continued)

OTHER PUBLICATIONS

Extended Search Report in European Appln. No. 22151132.2, dated May 2, 2022, 10 pages.

(Continued)

*Primary Examiner* — Daniel L Murphy
*Assistant Examiner* — Amie M Ndure
(74) *Attorney, Agent, or Firm* — Fish & Richardson P.C.

(57) ABSTRACT

In one aspect, there is provided a marine sensor platform that includes: a line having a plurality of slots that are spaced apart on the line, a plurality of sensor nodes, each sensor node configured to couple to each of the slots on the line, and each sensor node including at least one sensor, a power source coupled to the plurality of sensor nodes and configured to supply power to the plurality of sensor nodes on the line, and a controller coupled to the power source and the plurality of sensor nodes on the line, wherein the controller is configured to identify a type of the at least one sensor included in each of the sensor nodes when each of the sensor nodes is coupled to the respective slot on the line.

19 Claims, 3 Drawing Sheets

(56) References Cited

U.S. PATENT DOCUMENTS

| | | | |
|---|---|---|---|
| 11,089,227 B1* | 8/2021 | James | A01K 61/95 |
| 2007/0062696 A1* | 3/2007 | Wilson | E21B 47/135 |
| | | | 166/254.2 |
| 2012/0120767 A1* | 5/2012 | Vu | A61P 35/00 |
| | | | 367/25 |
| 2016/0041283 A1* | 2/2016 | Rokkan | G01V 1/3852 |
| | | | 405/168.1 |
| 2017/0150701 A1 | 6/2017 | Gilmore et al. | |
| 2019/0228218 A1 | 7/2019 | Barnaby et al. | |
| 2019/0302291 A1* | 10/2019 | Lolla | G01V 1/288 |
| 2019/0340440 A1 | 11/2019 | Atwater et al. | |
| 2020/0107524 A1 | 4/2020 | Messana et al. | |
| 2020/0155882 A1 | 5/2020 | Tohidi et al. | |
| 2020/0288678 A1 | 9/2020 | Howe et al. | |
| 2021/0274101 A1* | 9/2021 | James | G06T 7/50 |
| 2023/0333244 A1* | 10/2023 | Fonts | G01S 7/025 |

FOREIGN PATENT DOCUMENTS

| | | |
|---|---|---|
| EP | 2244934 | 11/2010 |
| EP | 3484283 | 5/2019 |
| JP | 2002171853 | 6/2002 |
| NO | 300401 | 5/1997 |
| NO | 20160199 | 8/2017 |
| WO | WO 1990/007874 | 7/1990 |
| WO | WO 1997/019587 | 6/1997 |
| WO | WO 2009/008733 | 1/2009 |
| WO | WO 2009/097057 | 8/2009 |
| WO | WO 2012/081990 | 6/2012 |
| WO | WO 2014/179482 | 11/2014 |
| WO | WO 2015/147391 | 10/2015 |
| WO | WO 2017/137896 | 8/2017 |
| WO | WO 2018/011744 | 1/2018 |
| WO | WO 2018/011745 | 1/2018 |
| WO | WO 2019/002881 | 1/2019 |
| WO | WO 2019/121851 | 6/2019 |
| WO | WO 2019/188506 | 10/2019 |
| WO | WO 2019/232247 | 12/2019 |
| WO | WO 2020/046524 | 3/2020 |
| WO | WO 2020/132031 | 6/2020 |
| WO | WO 2021/006744 | 1/2021 |
| WO | WO 2021/030237 | 2/2021 |
| WO | WO 2022/010815 | 1/2022 |
| WO | WO 2020/072438 | 4/2022 |

OTHER PUBLICATIONS

International Preliminary Report on Patentability in International Appln. No. PCT/US2020/059829, dated May 27, 2022, 11 pages.
International Search Report and Written Opinion in International Appln No. PCT/US2022/018651, dated Jun. 22, 2022, 14 pages.
International Search Report and Written Opinion in International Appln No. PCT/US2022/021683, dated Jun. 27, 2022, 14 pages.
International Search Report and Written Opinion in International Appln No. PCT/US2022/022250, dated Jul. 6, 2022, 15 pages.
International Search Report and Written Opinion in International Appln No. PCT/US2022/022492, dated Jun. 28, 2022, 13 pages.
International Search Report and Written Opinion in International Appln No. PCT/US2022/022589, dated Jul. 7, 2022, 12 pages.
International Search Report and Written Opinion in International Appln No. PCT/US2022/022837, dated Aug. 2, 2022, 14 pages.
International Search Report and Written Opinion in International Appln No. PCT/US2022/023831, dated Jul. 8, 2022, 13 pages.
International Search Report and Written Opinion in International Appln. No. PCT/US2020/059829, dated Feb. 25, 2021, 18 pages.
International Search Report and Written Opinion in International Appln. PCT/US2022/043344, dated Jan. 11, 2023, 21 pages.
Meidell et al., "FishNet: A Unified Embedding for Salmon Recognition," Thesis for Master's degree in Artificial Intelligence, Norwegian University of Science and Technology, Jun. 2019, 86 pages.
Moskvyak et al., "Robust Re-identification of Manta Rays from Natural Markings by Learning Pose Invariant Embeddings," CoRR, Feb. 2019, arXiv:1902.10847v1, 12 pages.
Qiu et al., "Improving Transfer Learning and Squeeze-and-Excitation Networks for Small-Scale Fine-Grained Fish Image Classification," IEEE Access, Dec. 2018, 6(31):78503-78512.
Stein et al., "Consistent melanophore spot patterns allow long-term individual recognition of Atlantic salmon *Salmo salar*," Journal of Fish Biology, Nov. 2017, 91(6):1699-1712.

* cited by examiner

DAISY CHAINED MARINE SENSOR PLATFORM

TECHNICAL FIELD

This specification relates to sensor systems for marine applications, and more specifically, to a daisy chained marine sensor platform that can be used to take different types of measurements underwater.

BACKGROUND

Taking measurements underwater in an accurate and cost-effective manner can be a challenging task. Such measurements may generally be required in different settings, one example of which is aquaculture, e.g., breeding, rearing, and harvesting of aquatic livestock under controlled conditions. Monitoring the feeding behavior of aquatic livestock by using a camera can be important for, e.g., determining the amount of feed that is being consumed by the livestock and modifying the feeding regiment accordingly. Measurements of temperature, water quality, and other aspects, can also provide an important insight into the aquaculture ecosystem.

Typically, monitoring of underwater conditions relies on mechanical winch-based systems, or line-based systems where sensors are manually submerged by a human operator. For example, a camera, or any other type of sensor, can be suspended on a winch line and moved underwater by engaging the motor that turns the winch. However, such systems facilitate observation only from one location at a time and therefore are subject to significant measurement latency. Furthermore, such systems present numerous challenges due to, e.g., the need to move bulky mechanical components in ocean environments, appearance of corrosion and damage due to wear-and-tear, operation at extreme temperatures and weather conditions, challenges related to maintenance in the underwater environment, risk of collisions with other hardware, and so on.

Accordingly, there exists a growing need for an intelligent sensor architecture that enables the monitoring of underwater environments in an effective and safe manner, while overcoming the aforementioned challenges and drawbacks associated with the typical winch-based systems.

SUMMARY

Implementations of the present disclosure include a marine sensor platform and a method for associating a type of sensor with a position of a sensor node in the marine sensor platform. More particularly, implementations of the present disclosure include an intelligent marine sensor platform having multiple interchangeable sensor nodes, each including one or more sensors. The sensor nodes are arranged in a daisy chain architecture and are coupled to, and spaced apart on, a single line. Each of the sensors, and sensor nodes, is individually addressable via a controller.

In a first aspect, there is provided a marine sensor platform that includes a line having multiple slots that are spaced apart on the line; multiple sensor nodes, where each sensor node is configured to couple to each of the slots on the line, and each sensor node includes at least one sensor; a power source coupled to multiple sensor nodes and configured to supply power to multiple sensor nodes on the line; and a controller coupled to the power source and multiple sensor nodes on the line, where the controller is configured to identify a type of the at least one sensor included in each of the sensor nodes when each of the sensor nodes is coupled to the respective slot on the line.

In some implementations, the sensor nodes are arranged in a daisy chain topology on the line.

In some implementations, the controller is further configured to (i) identify a position of each of the sensor nodes on the line, and (ii) store information that associates the type of the at least one sensor included in each of the sensor nodes with the position of each of the sensor nodes on the line.

In some implementations, the controller is further configured to (i) receive a winch command, and (ii) identify a sensor node of the plurality of sensor nodes that corresponds to the winch command.

In some implementations, the controller is further configured to (i) receive a sensor measurement request, (ii) identify one or more sensor nodes of the plurality of sensor nodes associated with the measurement request, and (iii) trigger the one or more sensors included in the one or more sensor nodes to obtain a measurement associated with the sensor measurement request.

In some implementations, triggering the one or more sensors included in the one or more sensor nodes to obtain the measurement comprises triggering the one or more sensors simultaneously.

In some implementations, the controller is further configured to (i) receive a power request from the sensor node, and (ii) trigger the power source to increase or decrease an amount of power supplied to the sensor node associated with the power request.

In some implementations, each of the sensor nodes is configured to have a different buoyancy.

In some implementations, the at least one sensor is configured to obtain a measurement of one or more of: a water quality, a depth, a temperature, a salinity, and an image of a scene.

In some implementations, each of the sensor nodes of the plurality of sensor nodes includes a different type of the at least one sensor.

In some implementations, the controller is configured to control power supplied to each of the plurality of sensor nodes independently.

In some implementations, the line is configured to have a buoyancy such that a length of the line is configured to extend substantially perpendicular to a water surface.

In some implementations, the sensor nodes are configured to be interchangeable with each other on the line.

In some implementations, the line is configured to have a variable thickness.

In some implementations, the power source comprises a renewable energy source.

In some implementations, the controller is further configured to distribute a total available power between the sensor nodes.

In a second aspect, there is provided a method that comprises obtaining, by a controller of a marine sensor platform that includes: (i) the controller, (ii) a line, (iii) multiple sensor nodes coupled to the line, where each of the sensor nodes includes at least one sensor, and (iv) a power source coupled to multiple sensor nodes and the controller, a request, identifying, by the controller, a type of the at least one sensor included in each of the sensor nodes when each of the sensor nodes is coupled to the respective slot on the line, identifying, by the controller, a position of each of the sensor nodes on the line, and storing, by the controller, information that associates the type of the at least one sensor included in each of the sensor nodes with the position of each of the sensor nodes on the line.

In some implementations, the method further includes receiving, by the controller, a sensor measurement request, identifying, by the controller, one or more sensor nodes of the plurality of sensor nodes associated with the measurement request, and triggering, by the controller, the one or more sensors included in the one or more sensor nodes to obtain a measurement associated with the sensor measurement request.

In some implementations, the method further includes receiving, by the controller, a power request from a sensor node of the plurality of sensor nodes, and triggering, by the controller, the power source to increase or decrease an amount of power supplied to the sensor node associated with the power request.

In a third aspect, there is provided one or more non-transitory computer-readable storage medium coupled to one or more processors that, when executed by the one or more processors, cause the one or more processors to perform operations in accordance with implementations of the methods provided herein.

Implementations of the present disclosure provide one or more of the following technical advantages and improvements over previously available solutions.

The daisy chained marine sensor platform includes multiple sensor nodes that are disposed and spaced apart on a single line. The sensor nodes replace bulky mechanical components that are typically required with conventional marine sensor systems making the platform significantly easier to install. Furthermore, the daisy chain topology and configuration of the platform enables ease of integration into existing underwater systems.

The platform is reconfigurable in that the underwater line on which the sensor nodes are disposed can be arranged in any appropriate manner with respect to the underwater environment, and the sensor nodes can be easily attached to, or detached from, the line, and are interchangeable. Moreover, each of the sensor nodes is able to support one or multiple sensors of the same, or different, type. For example, in aquaculture applications, the line with the sensor nodes can spiral around the pen that contains aquatic livestock, or it can be disposed vertically down the water column inside the pen. The highly reconfigurable nature of the platform enables a degree of flexibility and versatility that is not typically possible with conventional underwater sensor systems.

Instead of having to move bulky mechanical components to obtain measurements in different locations underwater, leading to significant measurement latency and wear-and-tear, as is the case with conventional winch-based systems, the platform can remain substantially stationary and each of the sensors in the sensor nodes can be triggered to take a measurement independently. For example, instead of moving a winch-based camera from point A to point B, the platform can intelligently convert the winch commands to corresponding locations (or identifications) of sensor nodes and trigger the respective one or more sensors coupled to the sensor nodes on demand, e.g., without the need to move the sensor from point A to point B to obtain the respective measurements. This enables the intelligent sensor platform to virtually eliminate measurement latency, thereby significantly improving the measurement accuracy while reducing the risk of collision damage and wear-and-tear associated with mechanically-movable sensor systems.

Moreover, simultaneously triggering one or more sensors coupled to multiple sensor nodes enables simultaneous acquisition of measurement data at multiple locations with respect to the water column, which is not typically possible with conventional winch-based systems. In response to a measurement request, the platform can intelligently select the right type (or multiple types) of sensor associated with the measurement request and trigger the sensor (or multiple sensors) to obtain the measurement, which facilitates diversification and customizability of underwater measurements through a single marine sensor platform.

The marine sensor platform can intelligently, individually, and automatically control and distribute power supplied to the sensor nodes on the line. For example, in response to a measurement request, the platform can automatically increase the amount of power supplied to the sensor, and the sensor node, associated with the measurement request. When a particular sensor, or sensor node, is not in use, the platform can minimize the amount of power supplied to this component. For example, the sensor nodes/sensors can be in a sleep mode (e.g., a low power mode) when they are not in use. In response to a command from the controller, e.g., a command that instructs a particular sensor node/sensor to take a measurement, the respective sensor node/sensor can switch from the sleep mode into a wake mode (e.g., a high power mode) such that it is able to draw enough power to obtain the measurement.

The sensor nodes/sensors can switch back to the sleep mode from the wake mode automatically, or in response to a corresponding command from the controller. Different sensor nodes are able to request additional power on demand. The system can further intelligently timeshare total available power between different sensors, which can be especially important when renewable energy sources are used as a source of power, e.g., the total supply of power varies with different weather and environmental conditions. Accordingly, the marine sensor platform is more energy efficient and environmentally friendly than the conventional underwater sensor systems.

BRIEF DESCRIPTION OF THE DRAWINGS

Like reference symbols in the various drawings indicate like elements.

DETAILED DESCRIPTION

Figure 1:
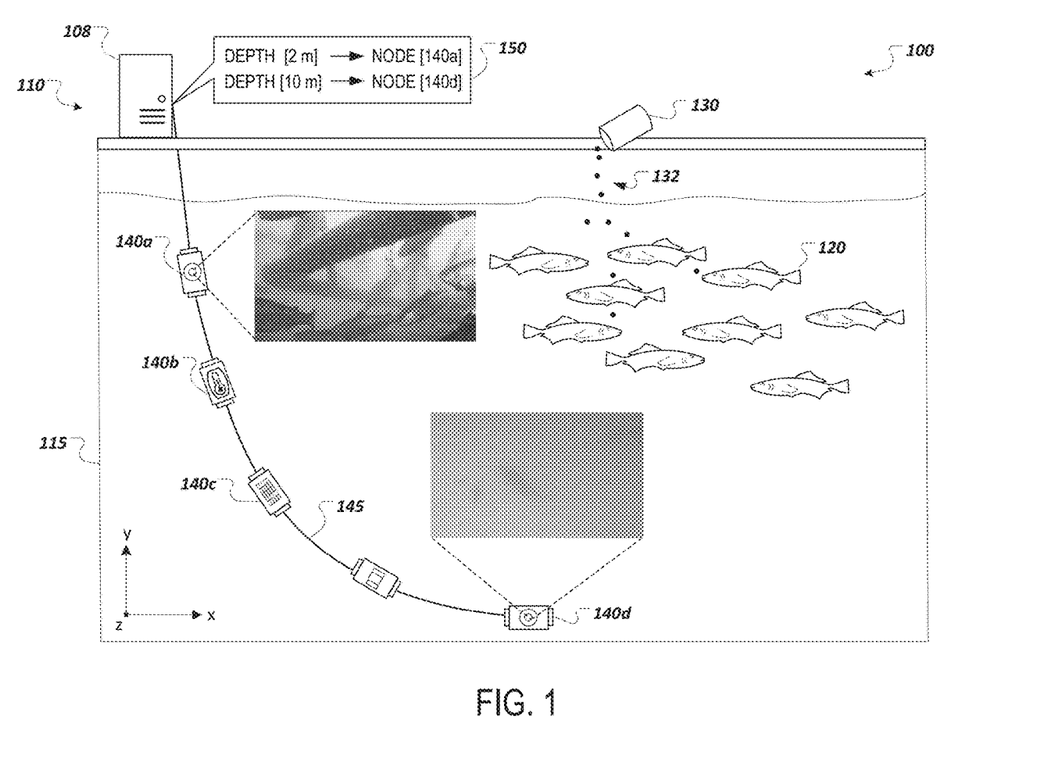
FIG. 1 is a schematic diagram of an example application of a marine sensor platform in accordance with implementations of the present disclosure.

FIG. 1 is a schematic diagram of an example application of a marine sensor platform 110 in accordance with implementations of the present disclosure. The marine sensor platform 110 is an intelligent multi-sensor architecture that is configured to obtain measurements underwater. Although FIG. 1 depicts the marine sensor platform 110 as being used to obtain measurements in aquafarming applications, the platform 110 can be applied in any other appropriate setting, e.g., any setting that requires obtaining measurements underwater.

FIG. 1 depicts an enclosure 115 that contains aquatic livestock. The livestock can be aquatic creatures, such as fish 120 swimming freely within the confines of the enclosure 115. In some implementations, the aquatic livestock 120 can include finfish, juvenile fish, koi fish, sharks, salmon, bass, and others. In addition to the aquatic livestock, the enclosure 115 contains water, e.g., seawater, freshwater, or rainwater, although the enclosure can contain any fluid that is capable of sustaining a habitable environment for the livestock. The enclosure 115 can further include an aquatic feeding system 130 that delivers feeding pellets 132 to the fish 120. In the example application illustrated in FIG. 1, the marine sensor platform 110 is used for monitoring a feeding behavior of fish 120, e.g., to detect the feeding pellets 132 delivered by the feeding system 130.

In some implementations, the marine sensor platform 110 can be anchored to a structure such as a pier, a dock, or a buoy, instead of being confined within the enclosure 115. For example, the fish 120 can be free to roam in a body of water, and the marine sensor platform 110 can be used to obtain measurements within a certain area of the body of water. Generally, the platform 110 (e.g., one or both ends of a line 145) can be at least partially fixed in any appropriate manner.

The marine sensor platform 110 includes a controller 108, the line 145, and multiple sensor nodes 140 (140a, 140b, 140c) disposed and spaced apart on the line 145. The line 145 can include, e.g., multiple slots that are spaced apart on the line 145, and each of the sensor nodes 140 can couple to a respective slot. In particular, the sensor nodes 140 can be interchangeable between the slots on the line 145. The platform 110 further includes a power source coupled to the controller 108 and the line 145 and configured to deliver power to the controller 108, the one or more sensor nodes 140, and sensors, by means of, e.g., a power transmitter that is coupled to the line 145, or in any other appropriate manner. Although FIG. 1 shows the platform 110 with five sensor nodes 140, the platform 110 can include any appropriate number of sensor nodes 140, e.g., 10, 50, 100, etc. Each of the sensor nodes 140 can include one or multiple sensors that can be, e.g., of the same, or different, type. For example, a single sensor node can include a camera and a temperature sensor.

In some implementations, some of consecutive sensor nodes on the line can include a different type of sensor, e.g., nodes 140a and 140d can include a camera, node 140b can include a temperature sensor, and node 140c can include a salinity sensor. Generally, the sensor nodes 140 can include any appropriate number of sensors configured to measure any appropriate physical aspect of the underwater environment, e.g., water quality, salinity, temperature. The sensors can further include, e.g., a camera capable of capturing image and video data (e.g., a monocular, or a stereo camera), etc. The sensor nodes can additionally include any other appropriate hardware such as e.g., light sources, feeders for delivering feeding pellets to aquatic livestock, etc. Moreover, some of the sensor nodes can be configured for higher-throughput applications, when compared to the other sensor nodes, by including, e.g., additional acquisition and computing/processing components.

In some implementations, the line 145 can be attached to, e.g., the netting of the enclosure 115, or the bottom of the enclosure 115. In some implementations, instead of being fixedly attached, the line 145 can be configured to be positioned underwater substantially vertically with respect to the water surface, and at least one end of the line 145 can be configured to move freely underwater. For example, one end of the line 145 can be coupled to a buoyancy control component, e.g., a weight. In another example, each of the sensor nodes 140 coupled to the line 145 can have a different buoyancy component that can be, e.g., detachable and/or interchangeable between the sensor nodes 140.

The sensor nodes 140 can be arranged on the line 145 in a daisy chain architecture. A "daisy chain" architecture refers to a linear network topology where several devices are connected together in a linear series, instead of each device being independently connected to a controller by means of a separate and independent cable (e.g., as is the case in a star network topology). If the sensors are arranged in a star topology, there exists a high potential for crossing or tangling of lines and cables, especially in underwater environments due to, e.g., variable weather conditions and strong ocean currents. Furthermore, the installation of such systems is particularly complex. By contrast, the daisy chain sensor node architecture replaces typical long cables (e.g., those used in winch-based marine sensor systems) with a few shorter cables thereby facilitating simpler installation and eliminating the possibility of crossing and tangling of lines.

The controller 108 is configured to communicate with each of the sensor nodes 140, and the respective sensors, on the line 145. Specifically, the controller 108 can be configured to identify a type of sensor (e.g., camera, temperature salinity, etc.) included in each of the sensor nodes 140. For example, the controller 108 can send a request to a particular sensor node, e.g., sensor node 140a, and the sensor node 140a can respond to the request by sending an identification number of the camera included in the sensor node 140a back to the controller 108. Accordingly, the controller 108 can determine that the sensor node 140a includes the camera. However, the controller 108 can identify the type of sensor, or multiple sensors, included in each of the sensor nodes 140, in any other appropriate manner.

The controller 108 can further be configured to identify a position of each of the sensor nodes 140 on the line 145, and store information that associates the type of sensor (e.g., identified as described above) included in the sensor node with the respective position of the sensor node on the line 145. The information can be stored in a database that can be implemented in an internal memory of the controller 108, or in any other appropriate manner. The database can also be referred to as a node map. A "position" of a sensor node can refer to, e.g., a unique identification of the sensor node, a count of the sensor node on the line 145 (e.g., node one, node two, etc.), a depth of the sensor node with respect to the water surface or with respect to the length of the line 145 (e.g., 1 meter from the end of the line 145, 2 meters from the end of the line 145, etc.), or any other appropriate aspect that enables locating the sensor node underwater.

For example, the controller 108 can communicate with the sensor node 140a and identify that it is coupled to a slot on the line 145 that is positioned 2 meters from the end of the line 145. Further, the controller 108 can identify that the sensor node 140a includes a camera. Accordingly, the controller can store information that associates the position of the sensor node 140a, e.g., 2 meters, with the type of sensor, e.g., the camera, in the sensor node map. Similarly, the controller 108 can identify that the sensor node 140d is positioned at 10 meters from the end of the line 145 and that it also includes a camera, and store information in the sensor node map that associates the position of the node 140d with the camera. The controller 108 can repeat this process any number of times, in response to a user-specified request, or automatically. In one example, the controller 108 can stop the identification process when the positions of all sensor nodes 140 on the line 145, and all the respective sensors, have been identified, and all the position/identification information has been stored in the sensor node map.

The controller 108 can also be configured to trigger, automatically or in response to a user-specified measurement request, one or more sensors coupled to one or more respective sensor nodes 140 to start/end taking a measurement. The measurement request can specify any appropriate type of information, e.g., a depth at which the measurement is desired, an identification number of a particular sensor node, one or more types of sensors, and/or any other appropriate information. In some implementations, the controller 108 can automatically and simultaneously trigger all sensors in all sensor nodes 140 to take a measurement once or at a particular time interval (e.g., every 5 seconds, every 1 hour, every 24 hours, etc.). This can facilitate, e.g., a time series of a complete measurement profile (temperature, salinity, etc.) of the entire water column. The time interval can be specified by a user of the platform 110, or can be determined automatically by the controller 108. For example, the controller 108 can send a measurement request to one or multiple sensor nodes 140 and sensors, and the respective sensors can begin/end taking a measurement in response to the measurement request. Generally, the controller 108 can be configured to trigger the sensors in the sensor nodes 140 to start/end taking the measurement in any appropriate manner.

In some implementations, the controller 108 can be configured to trigger one or more sensors to start/end taking a measurement in response to a user-specified measurement request. For example, the user can use an interface of a personal computing device (e.g., a computer) to input the measurement request that can be transmitted to the controller 108. In some implementations, the user can view the sensor node map in the interface of the device and interact with the map to select the desired sensor node and/or sensor for taking the measurement. The measurement request can include any appropriate type of information and/or instructions. In one example, the measurement request can specify, e.g., a winch-command that is typical for conventional winch-based measurement systems. The winch-command can specify, e.g., a depth to which the winch-based system should move the sensor with respect to the water surface (e.g., 2 meters) where it is desirable to obtain the measurement.

In response to receiving the measurement request, and by using the information stored in the sensor node map that associates the position of each of the sensor nodes 140 with the respective type of sensor included in each of the sensor nodes 140, the controller 108 can associate the winch command with the corresponding sensor node on the line 145, e.g., as illustrated by 150 in FIG. 1. That is, the winch-command specifying, e.g., 2 meters, corresponds to the sensor node 140a, because this sensor node is positioned at approximately 2 meters. In other words, the controller 108 can translate between commands that are typically used with conventional winch-based sensor systems and corresponding positions of the sensor nodes (and types of sensors) stored in the sensor node map. This facilitates ease of integration of the sensor platform 110 with conventional marine infrastructures.

After associating the user-specified measurement request with a particular sensor included in a particular sensor node, the controller 108 can trigger the sensor to perform the action associated with the measurement request, e.g., start/end taking the measurement specified in the request. By way of example, if the winch-command specifies a particular winch distance of 2 meters (and, optionally, a particular sensor type, e.g., a camera) the controller 108 can use the sensor node map to associate the distance of 2 meters with the sensor node 140a and trigger the camera included in the sensor node 140a to take the measurement (e.g., obtain image or video data, as shown in FIG. 1). The user-specified request can include any number of winch-commands and, optionally, information specifying any number and type of sensors. In another example, the winch-command can simultaneously specify winch distances of 2 meters and 10 meters, and the controller 108 can accordingly identify the corresponding sensor nodes as sensor nodes 140a and 140d, respectively, and trigger the sensors included in the respective sensor nodes 140a and 140d to start/end taking the measurement, as shown in FIG. 1.

In some implementations, the controller 108 can approximately determine which sensor node corresponds to a particular measurement request. For example, if the measurement request specifies a distance of e.g., 3 meters, the controller 108 can use the sensor node map to determine that the most proximate sensor node to 3 meters is the sensor node 140a, even though the sensor node 140a has a different position of 2 meters. In another example, the controller 108 can approximately determine which sensor node corresponds to a particular measurement request within the bounds of a particular threshold, e.g., a radius of 1 meter, such that if a sensor node in the sensor node map is positioned within the radius of 1 meter from, e.g., the exact distance specified in the measurement request, the controller 108 can determine that the sensor node is positioned substantially close to the distance specified in the measurement request and trigger the corresponding sensor coupled to that sensor node to take the measurement associated with the measurement request. The threshold can have any appropriate value and can be specified automatically, or by a user of the platform 110.

As described above, the marine sensor platform 110 includes the power source coupled to the line 145 and the controller 108. The controller 108 can be configured to operate the power source to supply power to each of the sensor nodes 140, and respective sensors, independently. For example, in response to an automatic, or a user-specified, power request, the controller 108 can operate the power source to perform an action associated with the power request, e.g., by increasing or decreasing an amount of power supplied to one or more sensor nodes 140 (and/or sensors included in the sensor nodes 140) associated with the power request. As another example, if the controller 108 triggers a particular sensor included in a sensor node to start obtaining a measurement, the sensor node can send a corresponding request to the controller 108 for additional power to be supplied to the sensor node. If the controller 108 determines that the request can be satisfied, the controller 108 can operate the power source to supply additional power to the sensor node. In some implementations, the controller 108 can be configured to operate the power source in order to timeshare the total available power. For example, the controller 108 can operate the power source to supply the power to each of the sensor nodes for a limited amount of time, or at particular time intervals, or in any other appropriate manner. The power source can be, e.g., a renewable energy source or any other appropriate source.

Figure 2:
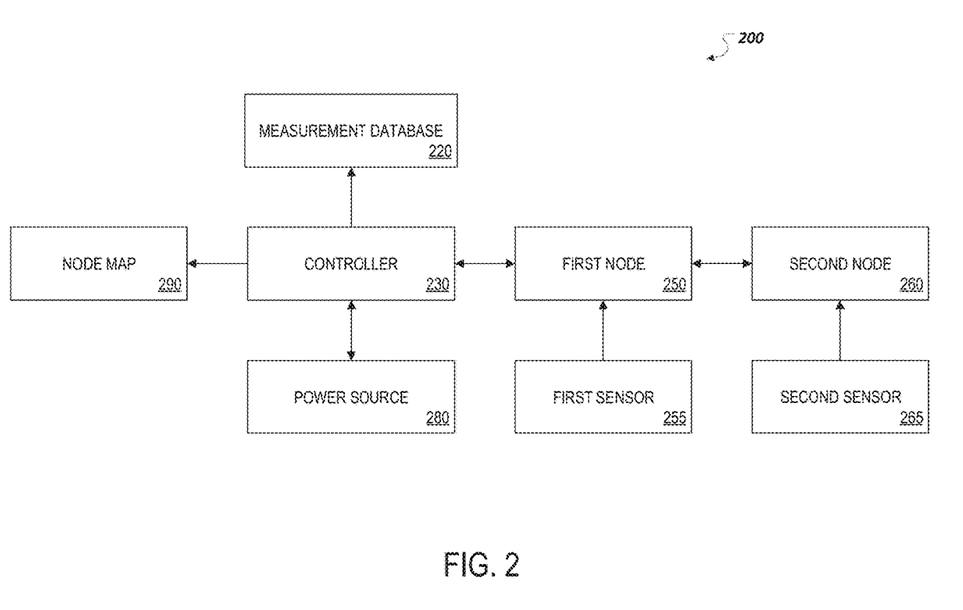
FIG. 2 is a block diagram of an example marine sensor platform in accordance with implementations of the present disclosure.

FIG. 2 is a block diagram of an example system 200 (e.g., the marine sensor platform system 110 in FIG. 1) in accordance with implementations of the present disclosure. The system 200 can be implemented by a combination of hardware, software, and firmware.

The system 200 can include sensor nodes 250 and 260, arranged in series (e.g., according to the daisy chain architecture, as described above) and communicatively coupled to a controller 230. Each of the sensor nodes includes a sensor 255, 265, respectively. Generally, the system 200 can include any number of sensor nodes arranged in series, and each of the sensor nodes 250, 260, can include any number of sensors 255, 265 of any appropriate type. As described above, the nodes 250, 260 can further include additional hardware such as, e.g., light sources, etc.

The controller 230 can be configured to identify a type of sensor included in each of the sensor nodes. For example, the controller 230 can send a request to the first sensor node 250, and in response to the request, the first sensor node 250 can send information that identifies the type of the first sensor 255 (e.g., a camera) included in the first sensor node 250. The information can generally be of any appropriate type, as long as it identifies the type of sensor. The controller can store this information in a node map 290 that is communicatively coupled to the controller 230 and can be implemented as, e.g., a database in an internal memory of the system 200. For example, the controller 230 can register in the node map 290 that the first sensor 255 included in the first node 250 is a camera, and that the second sensor 265 included in the second node 260 is a temperature sensor.

The controller 230 can further be configured to identify a position of each of the sensor nodes 250, 260 and store information that associates the position of the sensor nodes 250, 260 with the respective types of sensors 255, 265 in the node map 290. As described above, a "position" of a sensor node refers to information that locates the sensor node underwater. Such information can include, e.g., a depth of the sensor node with respect to the water surface, a distance of the sensor node from the end of the line, or any other appropriate type of positional information. The controller 230 can determine the respective positions of each of the sensor nodes 250, 260 and store the information in the node map 290. For example, the node map 290 can specify, e.g., first node 250, first sensor 255=camera, position=2 meters; second node 260, second sensor 265=temperature, position=4 meters, etc. Accordingly, the controller 230 can populate the node map 290 with information that specifies the types of sensors in sensor nodes, and respective positions of sensor nodes included in the system 200. The node map 290 can additionally include any type of metadata about identity, characteristics, and/or visual appearance such as size, configuration, and different orientations, calibration information, of the sensor nodes and/or sensors included in the system 200.

The system 200 can further include a measurement database 220 that can be implemented in, e.g., the internal memory of the system 200, and is communicatively coupled to the controller 230. As described above, in response to an automatic or user-specified measurement request, the controller 230 can use information stored in the node map 290 to identify, e.g., the best sensor node/sensor for obtaining the measurement associated with the measurement request. For example, if the measurement request specifies that it is desirable to obtain image and video data at a depth of 1 meter, the controller 230 can use the information stored in the node map 290 and determine that the best sensor node for obtaining this measurement is the first sensor node 250, because it is positioned substantially close to the depth of 1 meter within a particular threshold (e.g., at a depth of 2 meters), and it includes a camera. Accordingly, the controller 230 can trigger the camera in the first sensor node 250 to obtain image and video data, receive the image and video data from the first sensor node 250, and store it in the measurement database 220. Generally, the controller 230 can trigger (e.g., simultaneously) any number of sensors included in any number of sensor nodes to start/end taking the measurement at any appropriate time interval and in any appropriate manner.

The controller 230 can use the information stored in the measurement database 220 in any appropriate matter. In one example, in aquaculture applications, the controller 220 can use image and video data obtained by one or more cameras included in one or more respective sensor nodes to perform image recognition to identify, e.g., the number of feeding pellets that can be seen in the image and video data. Accordingly, the controller 230 can make an inference about the feeding behavior of fish. The aforementioned aquaculture applications are provided for illustrative purposes only, and the measurements obtained by the system 200 can be used in any other appropriate manner. Furthermore, in some implementations, one or more sensors included in the sensor nodes can continuously obtain measurements and continuously provide the measurements to the controller 230 in a data stream. The controller 230 can thereby continuously store the data in the measurement database 220, analyze the data, and in response to the analysis trigger one or more components of the system 200 to perform a particular action, e.g., trigger the first sensor 255 to stop obtaining the data, switch from obtaining the measurement with the first sensor 255 included in the first sensor node 250 to obtaining the measurement with the second sensor 265 included in the second sensor node 260, or any other appropriate action.

The system 200 further includes a power source 280 communicatively coupled to the controller 230. The controller 230 can manage the power supplied to different components of the system 200 by sending a power request (automatically or in response to an input from a user of the system 200) to the power source 280 and triggering the power source 280 to perform an action associated with the power request. In one example, the power source 280 can be configured to supply a minimum amount of power (e.g. less than, or equal to, 50 Watts) to all the sensor nodes in the system 200 such that they are able to boot up and register themselves on the node map 290, as described above. In some implementations, a sensor node can send a power request to the controller 230 to, e.g., request an additional amount of power from the power source 280. In response, the controller 230 can determine if the additional amount of power is available from the power source 280, and if so, trigger the power source 280 to supply the additional power to the respective sensor node. This can allow the sensor nodes to share the total available power in an intelligent manner, which can be particularly useful when the source of power is renewable, e.g., solar power, wind power etc., because the total amount of available energy can vary depending on the season and other factors.

In some implementations, the sensor nodes can be swapped according to a particular application or demand of the system 200. For example, the first sensor node 255 that includes the first sensor 255 that is a camera can be swapped for a different sensor node that includes a different sensor, e.g., a temperature sensor. If the sensor nodes are swapped, the system 200 can repeat the process of identifying the type of sensor included in a particular sensor node, and the position of the respective sensor node, in order to update the node map 290. This makes the system 200 highly intelligent, customizable and versatile, and applicable in many different settings and in variable weather conditions.

Figure 3:
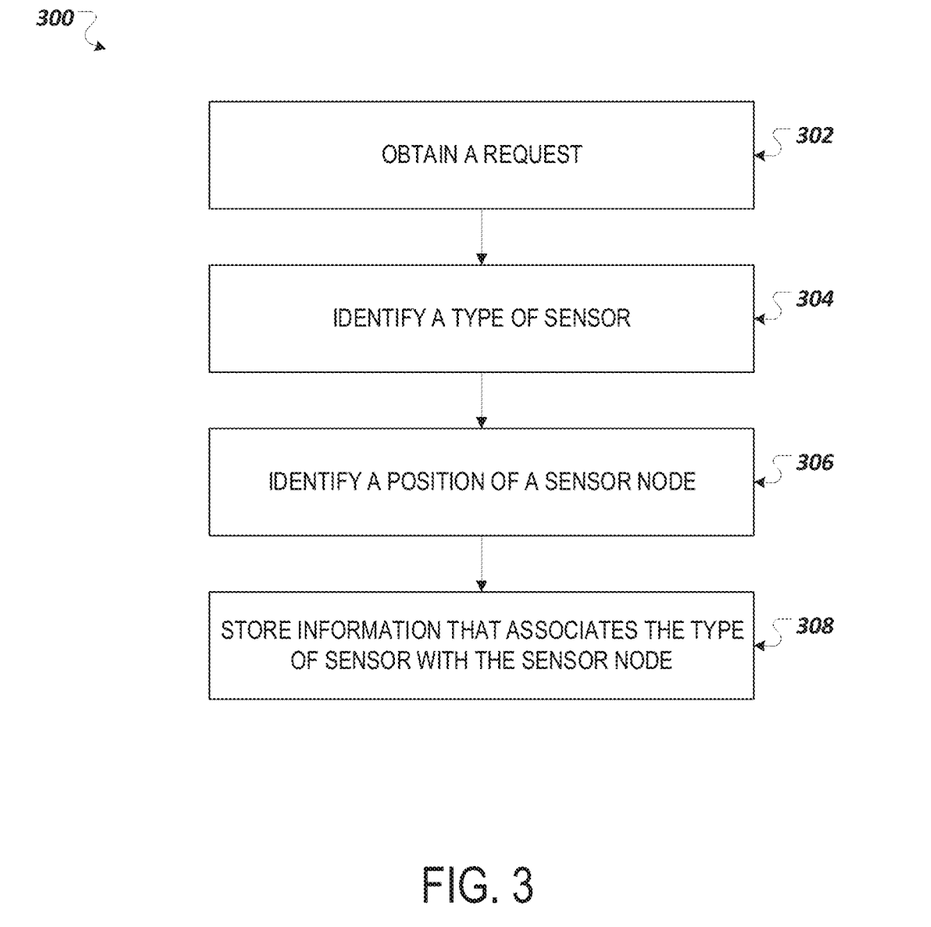
FIG. 3 is a flow diagram of an example process that can be executed in accordance with implementations of the present disclosure.

FIG. 3 is a flow diagram of an example process 300 that can be executed in accordance with the implementations of the present disclosure. The process 300 can associate a sensor node with a type of sensor in a marine sensor platform (e.g., the platform 110 in FIG. 1, or the platform system 200 in FIG. 2). For convenience, the process will be described as being performed by a system that can be, e.g., the platform 110 described above with reference to FIG. 1, or the system 200 described above with reference to FIG. 2.

The system obtains, by a controller of a marine sensor platform that includes: (i) the controller, (ii) a line, (iii) a plurality of sensor nodes coupled to the line, wherein each of the sensor nodes includes at least one sensor, and (iv) a power source coupled to the plurality of sensor nodes and the controller, a request (302). In some implementations, the measurement request can be obtained automatically, or in response to a user-specified request. In particular, a user of the marine sensor platform can input the request through an interface of a computing device (e.g., a computer, a tablet etc.) that is coupled to the marine sensor platform, and the request can be sent to the controller. In some implementations, the controller can obtain the request automatically, e.g., at a particular time interval.

The system identifies, by the controller, a type of the at least one sensor included in each of the sensor nodes when each of the sensor nodes is coupled to the respective slot on the line (304). As described above, the types of sensors can include, e.g., a camera, a temperature sensor, a salinity sensor, or any other appropriate sensor. In some implementations, each of the sensor nodes can be configured to have a different buoyancy, and the sensor nodes can be arranged in a daisy chain architecture on the line. Each of the sensor nodes can include multiple sensors that can be of the same, or different, type. The sensors can be chosen according to a particular application of the marine sensor platform, and can be reconfigured by interchanging the sensor nodes on the line.

The system identifies, by the controller, a position of each of the sensor nodes on the line (306). The position can represent, e.g., a location of the sensor node with respect to the water surface, or with respect to an end of the line, or any other appropriate positional aspect of the sensor nodes.

The system stores, by the controller, information that associates the type of the at least one sensor included in each of the sensor nodes with the position of each of the sensor nodes on the line (308). As described above, the system can store the information in the node map. The controller of the platform can use the node map to associate a particular sensor node/sensor with a measurement request in order to, e.g., identify the best, or optimal, sensor node/sensor for obtaining the measurement specified in the measurement request.

In some implementations, the process can further include receiving, by the controller of the marine sensor platform, a sensor measurement request, identifying, by the controller, one or more sensor nodes associated with the measurement request, and triggering, by the controller, the one or more sensors included in the one or more sensor nodes to obtain the measurement associated with the sensor measurement request.

In some implementations, the process can further include receiving, by the controller of the marine sensor platform, a power request from a sensor node, and triggering the power source to increase or decrease an amount of power supplied to the sensor node associated with the power request.

The features described may be implemented in digital electronic circuitry, or in computer hardware, firmware, software, or in combinations of them. The apparatus may be implemented in a computer program product tangibly embodied in an information carrier (e.g., in a machine-readable storage device) for execution by a programmable processor; and method steps may be performed by a programmable processor executing a program of instructions to perform functions of the described implementations by operating on input data and generating output. The described features may be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that may be used, directly or indirectly, in a computer to perform a certain activity or bring about a certain result. A computer program may be written in any form of programming language, including compiled or interpreted languages, and it may be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. Elements of a computer may include a processor for executing instructions and one or more memories for storing instructions and data. Generally, a computer may also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory may be supplemented by, or incorporated in, application-specific integrated circuits (ASICs).

To provide for interaction with a user, the features may be implemented on a computer having a display device such as a cathode ray tube (CRT) or liquid crystal display (LCD) monitor for displaying information to the user and a keyboard and a pointing device such as a mouse or a trackball by which the user may provide input to the computer.

The features may be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system may be connected by any form or medium of digital data communication such as a communication network. Examples of communication networks include, e.g., a local area network (LAN), a wide area network (WAN), and the computers and networks forming the Internet.

The computer system may include clients and servers. A client and server are generally remote from each other and typically interact through a network, such as the described one. The relationship of client and server arises by virtue of computer programs running on the respective computers and having a client-server relationship to each other.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims.

A number of implementations of the present disclosure have been described. Nevertheless, it will be understood that various modifications may be made without departing from the spirit and scope of the present disclosure. Accordingly, other implementations are within the scope of the following claims.

The invention claimed is:

1. A marine sensor platform comprising:
   a line having a plurality of slots that are spaced apart on the line and that can each support a removable sensor node;
   a plurality of the removable sensor nodes that are arranged on the line in a daisy chain, each sensor node configured to removably couple to each of the slots on the line, and each sensor node including at least one sensor;
   a power source coupled to the plurality of sensor nodes and configured to supply power to the plurality of sensor nodes on the line; and
   a controller coupled to the power source and the plurality of sensor nodes on the line, wherein the controller is configured to, when each of the removable sensor nodes is removably coupled to a respective slot on the line, transmit requests to the sensor nodes that are removably coupled to a respective slot on the line to request identifying information from each of the removable sensor nodes, and, based at least on the respective identifying information that is received from each of the removable sensor nodes that are removably coupled to a respective slot on the line, identify a type of the at least one sensor included in each of the removable sensor nodes.

2. The marine sensor platform of claim 1, wherein the controller is further configured to:
   (i) identify a position of each of the sensor nodes on the line; and
   (ii) store information that associates the type of the at least one sensor included in each of the sensor nodes with the position of each of the sensor nodes on the line.

3. The marine sensor platform of claim 1, wherein the controller is further configured to:
   (i) receive a winch command that is associated with relocating a device to a particular underwater position using a winch; and
   (ii) identify a sensor node of the plurality of sensor nodes that corresponds to the position associated with the winch command.

4. The marine sensor platform of claim 1, wherein the controller is further configured to:
   (i) receive a sensor measurement request;
   (ii) identify one or more sensor nodes of the plurality of sensor nodes associated with the measurement request; and
   (iii) trigger the one or more sensors included in the one or more sensor nodes to obtain a measurement associated with the sensor measurement request.

5. The marine sensor platform of claim 4, wherein triggering the one or more sensors included in the one or more sensor nodes to obtain the measurement comprises triggering the one or more sensors simultaneously.

6. The marine sensor platform of claim 1, wherein the controller is further configured to:
   (i) receive a power request from the sensor node; and
   (ii) trigger the power source to increase or decrease an amount of power supplied to the sensor node associated with the power request.

7. The marine sensor platform of claim 1, wherein each of the sensor nodes is configured to have a different buoyancy.

8. The marine sensor platform of claim 1, wherein the at least one sensor is configured to obtain a measurement of one or more of: a water quality, a depth, a temperature, a salinity, and an image of a scene.

9. The marine sensor platform of claim 1, wherein each of the sensor nodes of the plurality of sensor nodes includes a different type of the at least one sensor.

10. The marine sensor platform of claim 1, wherein the controller is configured to control power supplied to each of the plurality of sensor nodes independently.

11. The marine sensor platform of claim 1, wherein the line is configured to have a buoyancy such that a length of the line is configured to extend substantially perpendicular to a water surface.

12. The marine sensor platform of claim 1, wherein the sensor nodes are configured to be interchangeable with each other on the line.

13. The marine sensor platform of claim 1, wherein the line is configured to have a variable thickness.

14. The marine sensor platform of claim 1, wherein the power source comprises a renewable energy source.

15. The marine sensor platform of claim 1, wherein the controller is further configured to distribute a total available power between the sensor nodes.

16. A method comprising:
   obtaining, by a controller of a marine sensor platform that includes: (i) the controller, (ii) a line, (iii) a plurality of removable sensor nodes removably coupled to the line, wherein each of the sensor nodes includes at least one sensor, and (iv) a power source coupled to the plurality of removable sensor nodes and the controller, a request;
   transmitting, by the controller, requests to the plurality of removable sensor nodes that are removably coupled to a respective slot on the line to request identifying information from each of the removable sensor nodes;
   identifying, by the controller and based at least on the respective identifying information that is received from each of the removable sensor nodes that are removably coupled to a respective slot on the line, a type of the at least one sensor included in each of the sensor nodes when each of the sensor nodes is coupled to the respective slot on the line;
   identifying, by the controller and based at least on the respective identifying information that is received from each of the removable sensor nodes that are removably coupled to a respective slot on the line, a position of each of the removable sensor nodes on the line; and
   storing, by the controller, information that associates the type of the at least one sensor included in each of the removable sensor nodes with the position of each of the removable sensor nodes on the line.

17. The method of claim 16, further comprising:
   receiving, by the controller, a sensor measurement request;
   identifying, by the controller, one or more sensor nodes of the plurality of sensor nodes associated with the measurement request; and triggering, by the controller, the one or more sensors included in the one or more sensor nodes to obtain a measurement associated with the sensor measurement request.

18. The method of claim 16, further comprising:
receiving, by the controller, a power request from a sensor node of the plurality of sensor nodes; and
triggering, by the controller, the power source to increase or decrease an amount of power supplied to the sensor node associated with the power request.

19. One or more non-transitory computer-readable storage medium coupled to one or more processors that, when executed by the one or more processors, cause the one or more processors to perform operations comprising:
obtaining, by a controller of a marine sensor platform that includes: (i) the controller, (ii) a line, (iii) a plurality of removable sensor nodes removably coupled to the line, wherein each of the sensor nodes includes at least one sensor, and (iv) a power source coupled to the plurality of removable sensor nodes and the controller, a request;
transmitting requests to the plurality of removable sensor nodes that are removably coupled to a respective slot on the line to request identifying information from each of the removable sensor nodes;
identifying, based at least on the respective identifying information that is received from each of the removable sensor nodes that are removably coupled to a respective slot on the line, a type of the at least one sensor included in each of the sensor nodes when each of the sensor nodes is coupled to the respective slot on the line;
identifying, based at least on the respective identifying information that is received from each of the removable sensor nodes that are removably coupled to a respective slot on the line, a position of each of the removable sensor nodes on the line; and
storing information that associates the type of the at least one sensor included in each of the removable sensor nodes with the position of each of the removable sensor nodes on the line.

* * * * *

UNITED STATES PATENT AND TRADEMARK OFFICE
CERTIFICATE OF CORRECTION

| | | |
|---|---|---|
| PATENT NO. | : 12,375,310 B2 | Page 1 of 1 |
| APPLICATION NO. | : 17/507619 | |
| DATED | : July 29, 2025 | |
| INVENTOR(S) | : Andrew Rossignol et al. | |

It is certified that error appears in the above-identified patent and that said Letters Patent is hereby corrected as shown below:

On the Title Page

Column 1, Line 1 (Applicant):
Delete "TidalX AI Inc," and insert -- TidalX AI Inc., --.

Signed and Sealed this
Seventh Day of October, 2025

John A. Squires
*Director of the United States Patent and Trademark Office*